United States Patent
Chen et al.

(10) Patent No.: US 10,214,483 B2
(45) Date of Patent: Feb. 26, 2019

(54) TITANIUM-SILICALITE MOLECULAR SIEVE, METHOD FOR PREPARING THE SAME AND METHOD FOR PREPARING CYCLOHEXANONE OXIME USING THE MOLECULAR SIEVE

(71) Applicant: China Petrochemical Development Corporation, Taipei (TW)

(72) Inventors: Ya-Ping Chen, Taipei (TW); Cheng-Fa Hsieh, Taipei (TW); Pin-To Yao, Taipei (TW); Chien-Chang Chiang, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 209 days.

(21) Appl. No.: 15/241,947

(22) Filed: Aug. 19, 2016

(65) Prior Publication Data

US 2016/0355467 A1    Dec. 8, 2016

Related U.S. Application Data

(62) Division of application No. 13/350,045, filed on Jan. 13, 2012, now Pat. No. 9,434,683.

(30) Foreign Application Priority Data

Aug. 11, 2011    (TW) .............................. 100128649 A

(51) Int. Cl.
| | | |
|---|---|---|
| *C01B 37/00* | (2006.01) | |
| *B01J 29/89* | (2006.01) | |
| *C07C 249/04* | (2006.01) | |
| *C07C 251/44* | (2006.01) | |
| *B01J 29/87* | (2006.01) | |
| *C01B 39/08* | (2006.01) | |
| *C01B 39/06* | (2006.01) | |

(52) U.S. Cl.
CPC ............. *C07C 249/04* (2013.01); *B01J 29/89* (2013.01); *C01B 37/005* (2013.01); *C07C 251/44* (2013.01); *B01J 29/87* (2013.01); *B01J 2229/183* (2013.01); *C01B 39/06* (2013.01); *C01B 39/082* (2013.01); *C01B 39/085* (2013.01); *C07C 2601/14* (2017.05)

(58) Field of Classification Search
CPC ......... B01J 29/89; B01J 29/87; C01B 39/085; C01B 39/087; C01B 39/082; C01B 39/065; C07C 249/04; C07C 251/44
See application file for complete search history.

(56) References Cited

U.S. PATENT DOCUMENTS

| | | |
|---|---|---|
| 4,968,842 A | 11/1990 | Padovan et al. |
| 5,227,525 A | 7/1993 | Tonti et al. |
| 5,312,987 A | 5/1994 | Mantegazza et al. |
| 6,828,459 B2 | 12/2004 | Oikawa et al. |
| 8,962,872 B2 | 2/2015 | Hsu et al. |

FOREIGN PATENT DOCUMENTS

| | | | |
|---|---|---|---|
| CN | 103288678 A | * 2/2012 | .............. B01J 29/89 |
| EP | 226257 A2 | 6/1987 | |
| EP | 226258 A2 | 6/1987 | |
| EP | 266825 A1 | 5/1988 | |

* cited by examiner

*Primary Examiner* — David M Brunsman
(74) *Attorney, Agent, or Firm* — Mintz Levin Cohn Ferris Glovsky and Popeo, P.C.; Peter F. Corless; Joohee Lee

(57) ABSTRACT

The present invention provides a titanium-silicalite molecular sieve and a method for preparing the same. The method includes the steps of preparing a mixture of a titanium source, a silicon source, a metal source selected from IIA to IVA elements and a template agent; heating the mixture to form a gel mixture; heating the gel mixture in a water bath; and calcining the gel mixture after the gel mixture in the water bath to form the titanium-silicalite molecular sieve. The present invention further provides a method for preparing cyclohexanone oxime by using the titanium-silicalite molecular sieve as the catalyst which results in high conversion rate, high selectivity and high usage efficiency of hydrogen peroxide.

6 Claims, 1 Drawing Sheet

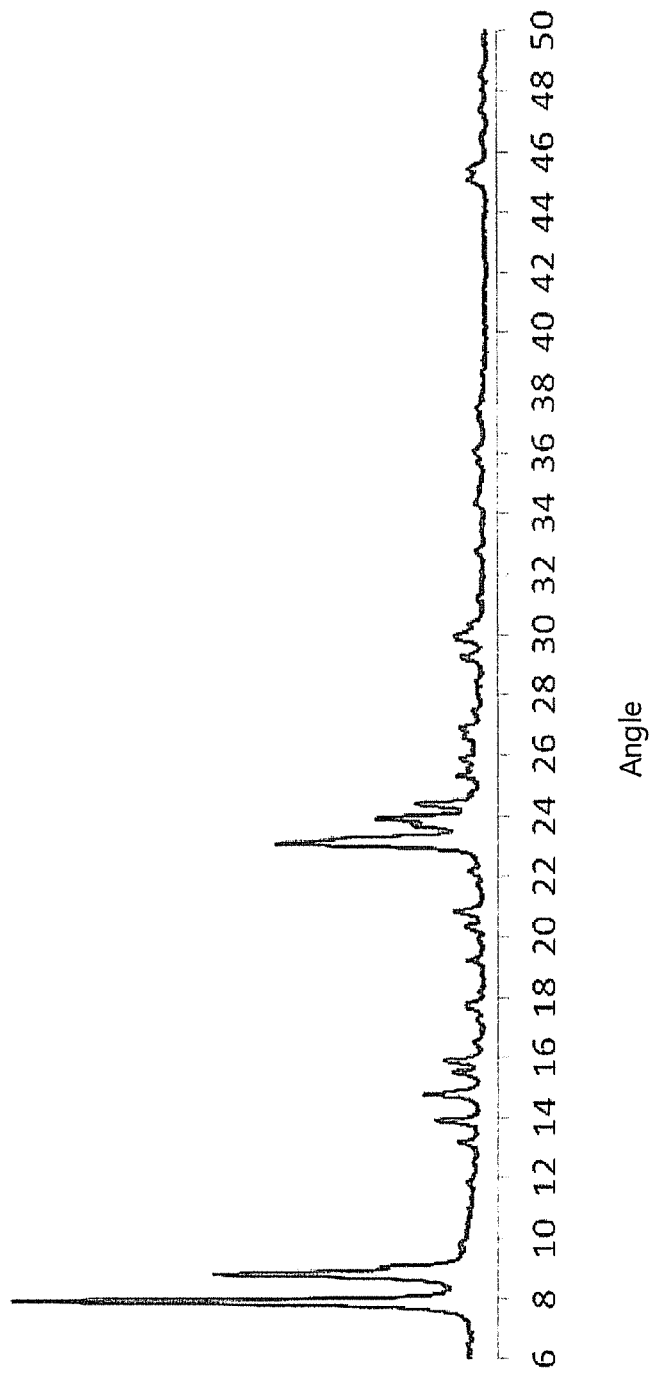

TITANIUM-SILICALITE MOLECULAR SIEVE, METHOD FOR PREPARING THE SAME AND METHOD FOR PREPARING CYCLOHEXANONE OXIME USING THE MOLECULAR SIEVE

CROSS-REFERENCES TO RELATED APPLICATIONS

This application is a divisional of U.S. application Ser. No. 13/350,045, filed Jan. 13, 2012, and issued as U.S. Pat. No. 9,434,683 on Sep. 6, 2016, which claims under 35 U.S.C. § 119(a) the benefit of priority of Taiwanese Application No. 100128649, filed Aug. 11, 2011, the entire contents of which are incorporated herein by reference.

BACKGROUND OF THE INVENTION

1. Field of the Invention

The present invention relates to titanium-silicalite molecular sieves and methods for preparing the same, and more particular to, a titanium-silicalite molecular sieve having a metal selected from IIA to IVA elements and a method for preparing the same.

2. Description of the Prior Art

Crystalline titanium-silicalite molecular sieves are formed by incorporating titanium into the zeolite structure of silicon dioxide. TS-1 molecular sieves have the MFI structures, and TS-2 molecular sieves have the MEL structures. These molecular sieves are used in oxidation reactions such as ammoximation of cyclohexanone and hydroxylation of phenol which use hydrogen peroxide as the oxidant.

Cyclohexanone oxime is the intermediate of the preparation of amides. U.S. Pat. Nos. 4,968,842, 522,752, 5,312,987 and 6,828,459 disclose using cyclohexanone, ammonia and hydrogen peroxide to form cyclohexanone oxime. However, in such methods, the usage efficiency of hydrogen peroxide is about 89% to 90%. The usage efficiency of hydrogen peroxide cannot be improved for lowering the production cost.

EP226257, EP266825 and EP226258 disclose methods for preparing a titanium-silicalite molecular sieve having a metal. EP226258 discloses that the iron source is treated with ammonia to form a hydroxide precipitation, the hydroxide precipitation is washed by water, neutralized, filtered, dissolved in the template agent, mixed with the titanium-silicon solution, and then heated to form the molecular sieve. Such method is complicated. EP266825 discloses that the gallium source is dissolved in ethanol, then mixed with the titanium-silicon mixture and template agent solution, and heated to form the molecular sieve. However, the gallium mixed with the titanium source and the silicon source would result in the white turbid product. The white turbid product is dissolved in the template agent. The template agent is in an aqueous form, but the dissolution of titanium is different from the dissolution of silicon. Thus, the order of the molecular sieve is decreased and the catalyst property is thus destroyed. EP226257 discloses that the aluminum source is dissolved in the template agent, then mixed with the titanium-silicon solution, and heated to form the molecular sieve. Similarly, the aluminum source mixed with the titanium source and the silicon source would result in the white turbid product. The white turbid product is dissolved in the template agent. The template agent is in an aqueous form, but the dissolution of titanium is different from the dissolution of silicon. Thus, the order of the molecular sieve is decreased and the catalyst property is destroyed.

SUMMARY OF THE INVENTION

Hence, the present invention provides a method for simplifying the preparation of the molecular sieve and provides a method using the molecular sieve of the invention for preparing cyclohexanone oxime which enhances the ammoximation of cyclohexanone and improves the usage efficiency of hydrogen peroxide.

The present invention provides a method for preparing a titanium-silicalite molecular sieve. The method includes the steps of preparing a mixture of a titanium source, a silicon source, a metal source, a template agent and water, wherein the metal source is at least one selected from IIA to IVA elements, and the template agent is dissolved in an alcohol solvent; heating the mixture to form a gel mixture; heating the gel mixture in a water bath; and calcining the gel mixture after heating the gel mixture in the water bath to form the titanium-silicalite molecular sieve.

In the present invention, the template agent is dissolved in an alcohol solvent in a concentration of 5 wt % to 50 wt %, and the gel mixture is heated to remove the alcohol solvent. After removing the alcohol solvent, the gel mixture is mixed with water.

In the present invention, a molar ratio of the template agent to the silicon source is less than or equal to 0.5. The metal source is selected from the group consisting of an acidic metal salt, a metal alkoxide and a metal complex. Preferably, the metal source is dissolved in the water and to be in an aqueous form before being mixed with the titanium source, the silicon source and the template agent to form the gel mixture.

Further, in the method for preparing a titanium-silicalite molecular sieve, after forming the gel mixture, the gel mixture is mixed with water or colloidal silica; and the gel mixture mixed with the water or the colloidal silica is heated in the water bath.

Generally, the colloidal silica is silicon dioxide gel solution, and an amount of the silicon dioxide is 0.1 to 50 wt % of the colloidal silica. The weight ratio of the colloidal silica to the gel mixture is in a range of from 0.001:1 to 0.5:1.

In addition, the present invention further provides a titanium-silicalite molecular sieve, including a silicon oxide; a titanium oxide; and a metal oxide, wherein a metal of the metal oxide is at least one selected from IIA to IVA elements, a molar ratio of titanium to silicon is in a range of from 0.005 to 0.1; and a molar ratio of a metal of the metal oxide to the silicon is in a range of from 0.00001 to 0.05.

Moreover, the present invention provides a method for preparing cyclohexanone oxime. The method includes the step of performing a reaction of cyclohexanone, ammonia and hydrogen peroxide in the presence of a titanium-silicalite molecular sieve of the present invention as a catalyst and a solvent.

Hence, in the method of the present invention, the metal source selected from IIA to IVA elements is mixed with the titanium source, silicon source and the template agent before the gem mixture is formed, such that the titanium-silicalite molecular sieve of the present invention has the metal oxide. The method for preparing cyclohexanone oxime by using the titanium-silicalite molecular sieve of the present invention results in high conversion rate, high selectivity, and high usage efficiency of hydrogen peroxide.

BRIEFE DESCRIPTION OF THE DRAWINGS

FIG. 1 shows the X-ray spectrum of the catalyst prepared from Embodiment 8 of the present invention.

DETAILED DESCRIPTION OF THE INVENTION

The following specific embodiments are provided to illustrate the disclosure of the present invention. These and other advantages and effects can be easily understood by those skilled in the art after reading the disclosure of this specification.

The present invention provides a method for preparing a titanium-silicalite molecular sieve. The method includes the steps of preparing a mixture of a titanium source, a silicon source, a metal source, a template agent and water, wherein the metal source is at least one selected from IIA to IVA elements, and the template agent is dissolved in an alcohol solvent; heating the mixture to form a gel mixture; heating the gel mixture in a water bath; and calcining the gel mixture after heating the gel mixture in the water bath to form the titanium-silicalite molecular sieve.

Generally, the silicon source is mixed with the titanium source and the template agent, and then added with the metal source solution. In the present invention, the titanium source may be a tetraalkyl titanate such as tetraethyl titanate, tetraisopropyl titanate or tetrabutyl titanate. The silicon source is tetraalkyl silicate or polyethoxysiloxane such as tetramethyl silicate, tetraethyl silicate, tetrapropyl silicate or tetrabutyl silicate. The polyethoxysiloxane may be ES-28 (n=1-2), ES-32 (n=3-4) or ES-40 (n=4-5) (Colcoat CO.) In the present invention, the titanium source and the silicon source may not be limited to the above examples, and may be one or a combination of the above examples.

In the present invention, the template agent includes tetrapropylammonium hydroxide in an alcohol solution. For example, the template agent may be tetrapropylammonium bromide dissolved in an alcohol for the anion exchange resin process. The alcohol has 1 to 5 carbons such as methanol, ethanol, isopropanol, n-butanol or tert-butanol. The concentration of the template agent may be 5 wt % to 50 wt % and preferably 20 wt % to 40 wt %. The molar ratio of the template agent to the silicon is less than or equal to 0.5. In the present invention, the template agent is dissolved in the alcohol solvent to prevent of the titanium source and the silicon source dissolved in water at a different rate. As when the titanium source and silicon source are dissolved in water at a different rate, order of the molecular sieve will decrease which results in deterioration of the property of the catalyst, such as the reduction of the reaction yield. Further, the metal source may be dissolved in water, to be in an aqueous form before being mixed with the titanium source, the silicon source and the template agent, so as to avoid the conventional problems.

The metal source is selected from the group consisting of an acidic metal salt, a metal alkoxide and a metal complex. The metal source is dissolved in the water to be in an aqueous form before being mixed with the titanium source, the silicon source and the template agent. The metal may be one or more selected from IIA to IVA elements such as Al, Ga, In, Ba, Ge, Ca, Sn and Mg. Preferably, the acidic metal salt is a sulfate or hydrochlorate such as aluminium chloride hexahydrate, gallium sulfate hydrate, indium chloride tetrahydrate, barium chloride dihydrate, calcium chloride, stannic chloride pentahydrate, magnesium sulfate hydrate, etc. The metal alkoxide may be a gallium oxide. The molecular sieve prepared from such metal sources may be used for the preparation of cyclohexanone oxime to significantly improve the yield thereof. In the present invention, the yield of the cyclohexanone oxime is 18 folds higher than that using the catalyst disclosed in EP226257.

In the mixture of the titanium source, the silicon source, the metal source, the template agent and water, the molar ratio of the titanium to the silicon is in a range of from 0.005 to 0.1, preferably 0.015 to 0.08 and more preferably 0.02 to 0.05; the molar ratio of the metal to the silicon is in a range of from 0.00001 to 0.05, preferably 0.0003 to 0.03, and more preferably 0.0005 to 0.02; the molar ratio of the water to the silicon is in a range of from 10 to 80, preferably 20 to 60, and more preferably 30 to 50; and the molar ratio of the template agent to the silicon is in a range of from 0.1 to 0.5, preferably 0.15 to 0.45, and more preferably 0.2 to 0.4.

In the present invention, after the gel mixture is formed, the gel mixture is mixed with water or colloidal silica, and the gel mixture mixed with the water or the colloidal silica is heated in the water bath. Generally, the gel mixture is mixed with silicon dioxide gel solution, and the amount of the silicon dioxide is 0.1 to 50 wt % of the colloidal silica. The silicon dioxide gel solution may be Ludox AS-40, Ludox AS-30, Ludox TM-40, Ludox TM-50, Ludox AM-30, Ludox HS-30, Ludox HS-40 (DuPont) or SNOWTEX-40, SNOWTEX-50, SNOWTEX-C, SNOWTEX-N, SNOWTEX-20L, SNOWTEX-ZL, SNOWTEX-UP (Nissan Chemical Industries, Ltd.) Further, the weight ratio of the colloidal silica to the gel mixture is in a range of from 0.001:1 to 0.5:1.

In the present invention, the titanium-silicalite molecular sieve includes a silicon oxide, a titanium oxide, and a metal oxide, wherein the metal of the metal oxide is at least one selected from IIA to IVA elements; the molar ratio of the titanium to the silicon is in a range from 0.005 to 0.1; and the molar ratio of the metal of the metal oxide to the silicon is in a range of from 0.00001 to 0.05. The metal atoms of the transition metal oxide are positioned inside or outside the skeleton of the molecular sieve.

The present invention further provides a method for preparing cyclohexanone oxime. In this method, the titanium-silicalite molecular sieve of the present invention is used as the catalyst, and the reaction of cyclohexanone, ammonia and hydrogen peroxide is performed at 1 atm and 40 to 110° C., preferably 50 to 90° C., to form cyclohexanone oxime. The molar ratio of ammonia to cyclohexanone is in a range of from 1.2:1 to 2:1, preferably 1.4:1 to 1.8:1; and the molar ratio of hydrogen peroxide to cyclohexanone is in a range of from 0.7:1 to 2.5:1, preferably 0.9:1 to 1.5:1. The solvent may be a polar solvent such as an alcohol, a ketone or water. Preferably, the solvent may be tert-butanol. The amount of the catalyst may be 0.1 to 10%, and preferably 1 to 5%, of the total amount of the reactants.

In addition, the concentration of hydrogen peroxide may be 30 wt % to 70 wt %, and the hydrogen peroxide may be gradually added into the reaction system.

Comparative Example 1

In this embodiment, no metal source is used for preparing the titanium-silicalite molecular sieve.

A flask (500 ml) was nitrogen sealed under vacuum. 1.98 g of tetrabutyl titanate was added into the flask, and then cooled down to 5° C. Then, 20 g of anhydrous isopropanol was added and stirred. Upon temperature equilibrium, 30 g of tetraethyl silicate was dropped into the flask, and then stirred for 1 hour. 56 g (20 wt %) of tetrapropylammonium hydroxide solution was dropped into the flask, and then stirred. Then, the mixture was heated at 85° C. to remove alcohol, and added with water to form the gel mixture with a total weight of 100 g. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiments 1-9 provided various preparations of titanium-silicalite molecular sieves having various metal oxides.

Embodiment 1

Al-TS-1 Preparation (Catalyst A)

A flask (500 ml) was nitrogen sealed under vacuum. 1.98 g of tetrabutyl titanate was added into the flask, and then cooled down to 5° C. Upon temperature equilibrium, 30 g of tetraethyl silicate was dropped into the flask, and then stirred for 1 hour. 56.5 g (20 wt %) of tetrapropylammonium hydroxide isopropanol solution was dropped into the flask. 0.139 g of aluminium chloride hexahydrate was dissolved in 20 ml of water, and then this solution was dropped into the flask. Then, the mixture was stirred, then heated at 85° C. to remove alcohol, and added with water to form the gel mixture with a total weight of 100 g. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 2

Ga-TS-1 Preparation (Catalyst B)

A flask (500 ml) was nitrogen sealed under vacuum. 1.99 g of tetrabutyl titanate was added into the flask, and then cooled down to 5° C. Upon temperature equilibrium, 30.12 g of tetraethyl silicate was dropped into the flask, and then stirred for 1 hour. 56 g (20 wt %) of tetrapropylammonium hydroxide isopropanol solution was dropped into the flask. 0.25 g of gallium sulfate hydrate was dissolved in 20 ml of water, and then this solution was dropped into the flask. Then, the mixture was stirred, then heated at 85° C. to remove alcohol, and added with water to form the gel mixture with a total weight of 100 g. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 3

In-TS-1 Preparation (Catalyst C)

A flask (500 ml) was nitrogen sealed under vacuum. 1.95 g of tetrabutyl titanate was added into the flask, and then cooled down to 5° C. Upon temperature equilibrium, 30.3 g of tetraethyl silicate was dropped into the flask, and then stirred for 1 hour. 56.5 g (20 wt %) of tetrapropylammonium hydroxide isopropanol solution was dropped into the flask. 0.17 g of indium chloride tetrahydrate was dissolved in 20 ml of water, and then this solution was dropped into the flask. Then, the mixture was stirred, then heated at 85° C. to remove alcohol, and added with water to form the gel mixture with a total weight of 100 g. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 4

Ba-TS-1 Preparation (Catalyst D)

A flask (500 ml) was nitrogen sealed under vacuum. 1.98 g of tetrabutyl titanate was added into the flask, and then cooled down to 5° C. Upon temperature equilibrium, 30.1 g of tetraethyl silicate was dropped into the flask, and then stirred for 1 hour. 56.5 g (20 wt %) of tetrapropylammonium hydroxide isopropanol solution was dropped into the flask. 0.137 g of barium chloride dihydrate was dissolved in 20 ml of water, and then this solution was dropped into the flask. Then, the mixture was stirred, then heated at 85° C. to remove alcohol, and added with water to form the gel mixture with a total weight of 100 g. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 5

Ge-TS-1 Preparation (Catalyst E)

A flask (500 ml) was nitrogen sealed under vacuum. 1.97 g of tetrabutyl titanate was added into the flask, and then cooled down to 5° C. Upon temperature equilibrium, 30.08 g of tetraethyl silicate was dropped into the flask, and then stirred for 1 hour. 56.5 g (20 wt %) of tetrapropylammonium hydroxide isopropanol solution was dropped into the flask. 0.006 g of gallium oxide was dissolved in 20 ml of water, and then this solution was dropped into the flask. Then, the mixture was stirred, then heated at 85° C. to remove alcohol, and added with water to form the gel mixture with a total weight of 100 g. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 6

Ca-TS-1 (Catalyst F)

A flask (500 ml) was nitrogen sealed under vacuum. 2 g of tetrabutyl titanate was added into the flask, and then cooled down to 5° C. Upon temperature equilibrium, 30.14 g of tetraethyl silicate was dropped into the flask, and then stirred for 1 hour. 56.5 g (20 wt %) of tetrapropylammonium hydroxide isopropanol solution was dropped into the flask. 0.064 g of calcium chloride was dissolved in 20 ml of water, and then this solution was dropped into the flask. Then, the mixture was stirred, then heated at 85° C. to remove alcohol, and added with water to form the gel mixture with a total weight of 100 g. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 7

Sn-TS-1 Preparation (Catalyst G)

A flask (500 ml) was nitrogen sealed under vacuum. 2.1 g of tetrabutyl titanate was added into the flask, and then cooled down to 5° C. Upon temperature equilibrium, 30.4 g of tetraethyl silicate was dropped into the flask, and then stirred for 1 hour. 56.5 g (20 wt %) of tetrapropylammonium hydroxide isopropanol solution was dropped into the flask. 0.206 g of stannic chloride pentahydrate was dissolved in 20 ml of water, and then this solution was dropped into the flask. Then, the mixture was stirred, then heated at 85° C. to remove alcohol, and added with water to form the gel mixture with a total weight of 100 g. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 8

Mg-TS-1 Preparation (Catalyst H)

A flask (500 ml) was nitrogen sealed under vacuum. 2 g of tetrabutyl titanate was added into the flask, and then cooled down to 5° C. Upon temperature equilibrium, 30.18 g of tetraethyl silicate was dropped into the flask, and then stirred for 1 hour. 56.5 g (20 wt %) of tetrapropylammonium hydroxide isopropanol solution was dropped into the flask. 0.141 g of magnesium sulfate hydrate was dissolved in 20 ml of water, and then this solution was dropped into the flask. Then, the mixture was stirred, then heated at 85° C. to remove alcohol, and added with water to form the gel mixture with a total weight of 100 g. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst. As shown in FIG. 1, the molecular sieve of the present invention had the MFI structure. The molecular sieves in other embodiments of the present invention were all identified by the X-ray spectra.

Embodiment 9

Ga-TS-1 Preparation with Addition of Colloidal Silica (Catalyst I)

A flask (500 ml) was nitrogen sealed under vacuum. 1.97 g of tetrabutyl titanate was added into the flask, and then cooled down to 5° C. Upon temperature equilibrium, 30.144 g of tetraethyl silicate was dropped into the flask, and then stirred for 1 hour. 56.5 g (20 wt %) of tetrapropylammonium hydroxide isopropanol solution was dropped into the flask. 0.246 g of gallium sulfate hydrate was dissolved in 20 ml of water, and then this solution was dropped into the flask. Then, the mixture was stirred, then heated at 85° C. to remove alcohol, and added with 10.80 g of Ludox AS-40 and water to form the gel mixture with a total weight of 100 g. The gel mixture was sealed in a stainless steel can, and was heated at 180° C. for 120 hours. Then, the solid was separated from the liquid, and was cleaned with pure water to be neutral. The solid was dried at 100° C., and calcined at 500° C. for 8 hours, so as to obtain the catalyst.

Embodiment 10

The titanium-silicalite molecular sieves prepared from Comparative Example 1 and Embodiments 1-3 were respectively used as the catalyst for the preparation of cyclohexanone oxime.

0.55 g of the catalyst was placed in a flask, and added with 5 g of cyclohexanone, 28.5 g of tert-butanol and 4.7 g (28 wt %) of ammonia. The reaction system was equipped with a condensation tube and a stirring device. The temperature of the reaction system was heated to 60° C., and then 4.96 g of 35 wt % hydrogen peroxide solution (ketone:$H_2O_2$=1.0:1.0) was gradually added in 5 hours to perform the preparation of cyclohexanone oxime. Upon 1 hour after the introduction of hydrogen peroxide, the catalyst was separated from the reaction solution. Then, the reaction solution was analyzed. The results were shown in Table 1.

TABLE 1

| Molecular sieve catalyst | $X^a$ | $S^b$ | $X^c$ | $S^d$ |
|---|---|---|---|---|
| Comparative Example (TS-1) | 95.27% | 96.49% | 99.25% | 92.58% |
| Catalyst A | 96.73% | 97.65% | 99.67% | 94.72% |
| Catalyst B | 97.95% | 99.02% | 99.92% | 97.38% |
| Catalyst C | 95.80% | 97.13% | 99.35% | 93.93% |

$X^a$ = conversion rate of cyclohexanone = moles of consumed cyclohexanone/initial moles of cyclohexanone × 100%
$S^b$ = selectivity of cyclohexanone oxime = moles of produced cyclohexanone oxime/moles of consumed cyclohexanone × 100%
$X^c$ = conversion rate of hydrogen peroxide = moles of consumed hydrogen peroxide/initial moles of hydrogen peroxide × 100%
$S^d$ = selectivity of hydrogen peroxide = moles of produced cyclohexanone oxime/moles of consumed hydrogen peroxide × 100%

Embodiment 11

The titanium-silicalite molecular sieves prepared from Comparative Example 1, Embodiments 4-5 and Embodiment 9 were respectively used as the catalyst for the preparation of cyclohexanone oxime.

0.55 g of the catalyst was placed in a flask, and added with 5 g of cyclohexanone, 28.5 g of tert-butanol and 4.7 g (28 wt %) of ammonia. The reaction system was equipped with a condensation tube and a stirring device. The temperature of the reaction system was heated to 60° C., and then 5.20 g of 35 wt % hydrogen peroxide solution (ketone:$H_2O_2$=1.00:1.05) was gradually added in 5 hours to perform the preparation of cyclohexanone oxime. Upon 1 hour after the introduction of hydrogen peroxide, the catalyst was separated from the reaction solution. Then, the reaction solution was analyzed. The results were shown in Table 2.

TABLE 2

| Molecular sieve catalyst | $X^a$ | $S^b$ | $X^c$ | $S^d$ |
|---|---|---|---|---|
| Comparative Example (TS-1) | 99.17% | 98.03% | 99.52% | 92.95% |
| Catalyst D | 99.15% | 98.28% | 99.08% | 94.05% |
| Catalyst E | 99.35% | 99.02% | 99.27% | 94.33% |
| Catalyst I | 99.92% | 98.72% | 99.38% | 95.94% |

Embodiment 12

The titanium-silicalite molecular sieves prepared from Comparative Example 1 and Embodiments 6-8 were respectively used as the catalyst for the preparation of cyclohexanone oxime.

0.55 g of the catalyst was placed in a flask, and added with 5 g of cyclohexanone, 28.5 g of tert-butanol and 4.7 g (28 wt %) of ammonia. The reaction system was equipped with a condensation tube and a stirring device. The temperature of the reaction system was heated to 60° C., and then 5.35 g of 35 wt % hydrogen peroxide solution (ketone: $H_2O_2$=1.00:1.08) was gradually added in 5 hours to perform the preparation of cyclohexanone oxime. Upon 1 hour after the introduction of hydrogen peroxide, the catalyst was separated from the reaction solution. Then, the reaction solution was analyzed. The results were shown in Table 3.

TABLE 3

| Molecular sieve catalyst | $X^a$ | $S^b$ | $X^c$ | $S^d$ |
|---|---|---|---|---|
| Comparative Example (TS-1) | 99.22% | 98.02% | 99.31% | 90.58% |
| Catalyst F | 99.96% | 99.10% | 99.17% | 92.80% |
| Catalyst G | 99.60% | 99.09% | 99.23% | 92.12% |
| Catalyst H | 99.76% | 98.75% | 98.80% | 92.92% |

Accordingly, in the method of the present invention, the metal source is mixed with the titanium source, the silicon source and the template agent before the gel mixture is formed, such that the titanium-silicalite molecular sieve of the present invention has the metal oxide. The method for preparing cyclohexanone oxime by using the titanium-silicalite molecular sieve of the present invention results in high conversion rate, high selectivity, and high usage efficiency of hydrogen peroxide. Moreover, in comparison with the prior art, the preparation of cyclohexanone oxime by using the titanium-silicalite molecular sieve of the present invention has high yield. The yield of the preparation of cyclohexanone oxime by using the titanium-silicalite molecular sieve of the present invention is 18 folds of the yield of the preparation of cyclohexanone oxime by using the catalyst disclosed in EP226257, and 1.5 fold of the yield of the preparation of cyclohexanone oxime by using the catalyst disclosed in EP266825.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A method for preparing cyclohexanone oxime, comprising the step of:
performing a reaction of cyclohexanone, ammonia and hydrogen peroxide in the presence of a titanium-silicalite molecular sieve as a catalyst and a solvent, wherein the titanium-silicalite molecular sieve comprises a silicon oxide, a titanium oxide, and a metal oxide, wherein a metal of the metal oxide is at least one selected from IIA, IIIA, and IVA elements, with a molar ratio of titanium to silicon in a range of from 0.005 to 0.1 and a molar ratio of the metal to the silicon in a range of from 0.00001 to 0.05.

2. The method of claim 1, wherein a molar ratio of the ammonia to the cyclohexanone is in a range of from 1.1:1 to 2:1.

3. The method of claim 1, wherein a molar ratio of the hydrogen peroxide to the cyclohexanone is in a range of from 0.7:1 to 2.5:1.

4. The method of claim 1, wherein the solvent is one or more selected from the group consisting of an alcohol, a ketone and water.

5. The method of claim 4, wherein the solvent is tert-butanol.

6. The method of claim 1, wherein an amount of the titanium-silicalite molecular sieve is 0.1 to 10 wt % of a total weight of the cyclohexanone, the ammonia and the hydrogen peroxide.

* * * * *